United States Patent
Siegel

(10) Patent No.: US 9,938,648 B2
(45) Date of Patent: Apr. 10, 2018

(54) METHOD FOR THE SURFACE MODIFICATION OF PRODUCTS MADE OF LOW-ENERGY SYNTHETIC FIBERS

(75) Inventor: Rolf Siegel, Wuerzburg (DE)

(73) Assignee: Labor Fuer Molekulares Design, Wuerzburg (DE)

( * ) Notice: Subject to any disclaimer, the term of this patent is extended or adjusted under 35 U.S.C. 154(b) by 684 days.

(21) Appl. No.: 13/982,973

(22) PCT Filed: Feb. 2, 2012

(86) PCT No.: PCT/DE2012/000089
§ 371 (c)(1),
(2), (4) Date: Jul. 31, 2013

(87) PCT Pub. No.: WO2012/103876
PCT Pub. Date: Aug. 9, 2012

(65) Prior Publication Data
US 2013/0309480 A1 Nov. 21, 2013

(30) Foreign Application Priority Data

Feb. 3, 2011 (DE) .................. 10 2011 010 136

(51) Int. Cl.
*B05D 3/02* (2006.01)
*D04H 1/64* (2012.01)
*A61L 15/52* (2006.01)
*A61L 27/50* (2006.01)
*D06M 15/333* (2006.01)
*D06M 15/356* (2006.01)
*D06P 1/52* (2006.01)
*D06P 5/22* (2006.01)

(52) U.S. Cl.
CPC ............... *D04H 1/64* (2013.01); *A61L 15/52* (2013.01); *A61L 27/50* (2013.01); *D06M 15/333* (2013.01); *D06M 15/3568* (2013.01); *D06P 1/5228* (2013.01); *D06P 1/5292* (2013.01); *D06P 5/22* (2013.01); *Y10T 428/249921* (2015.04); *Y10T 428/249924* (2015.04)

(58) Field of Classification Search
CPC ...... A61L 15/52; A61L 27/50; D06M 15/333; D06M 15/3568; D04H 1/64; D06P 1/5228; D06P 1/5292; D06P 5/22; Y10T 428/249924; Y10T 428/249921
See application file for complete search history.

(56) References Cited

FOREIGN PATENT DOCUMENTS

DE 69716773 T2 7/2003
JP 2002029151 A * 1/2002
WO WO99/06622 A1 2/1999

OTHER PUBLICATIONS

English translation of the abstract of Toray JP50157696, 1975.*

* cited by examiner

*Primary Examiner* — Robert S Walters, Jr.
(74) *Attorney, Agent, or Firm* — McNees Wallace & Nurick LLC

(57) ABSTRACT

The invention relates to a wet chemical method for the surface modification of products made of low-energy synthetic fibers, to the products produced by the method and to the use of the products produced by the method. The material surface is permanently provided with functional groups by contact with an aqueous polyvinylalcohol solution containing silanol(ate) groups. Depending upon the design, the materials have a high water consumption or transmission capacity or exhibit a capillary activity. The range of uses for surface-modified materials is extended by the possibility of reacting the functional groups, inter alia, with biologically active components.

18 Claims, No Drawings

METHOD FOR THE SURFACE MODIFICATION OF PRODUCTS MADE OF LOW-ENERGY SYNTHETIC FIBERS

BACKGROUND OF THE INVENTION

The invention relates to a method for the surface modification of products made of low-energy synthetic fibres, to the products produced by the method and to the use of the products produced by the method.

The term "synthetic fibres" as it is used here refers to linear, thread-like macromolecules which, for example, can belong to the material classes of aramids, polyesters, polyamides, polyacrylates, polyacrylonitriles, polyurethanes, (per)fluorinated polyolefins, such as polytetrafluoroethylene or polyvinylidene(di)fluoride, polysulfones, polyimides, polyolefins etc., as well as co- or terpolymers thereof.

In the following the term "products made of low-energy synthetic fibres" refers to molded articles in 1 and/or 2-dimensional form. Articles in 1-dimensional form include, for example, filaments, monofilaments, multifilaments, fibres, threads, yarns, strings, rovings etc. Their diameter can be in the lower μm range or in the lower mm range, for example at 6 μm on the one hand or 3.4 mm on the other hand. The length can be in the mm range (staple fibres) or in the km range (filaments). The cross section of the fibres can be round, elliptical, triangular, rectangular, polygonal, star-shaped, lobular, cylindrical etc. The unmodified fibre surface may be rough or smooth. In mainly 2-dimensional form these are textile materials which exist as filament composite material such as tissue, knitted fabrics, fleece, nets, braids etc. or as fibre composite material such as non-wovens, felts, wadding etc. or as combinations of filament and fibre composite materials such as textile multilayer composites.

The area density is limited only by the technical feasibility and can range, for example, from 6 $g/m^2$ to 1,600 $g/m^2$. In particular in connection with surface modification(s), the term "material" is also used in the following for the abovementioned products made of synthetic fibres.

The term "surface modification" used here means that the surfaces of non-surface-modified materials differ from surface-modified materials in at least one of the following features:
- in the results of surface analysis using, for example, ESCA (Electron Spectroscopy for Chemical Analysis) or SIMS (Secondary Ion Mass Spectroscopy)
- in the wettability with water
- in the electrostatic properties
- in the chemical reactivity, e.g. in the ability to be dyed with water-soluble dyes The term "low-energy" as used here means that products made of low-energy synthetic fibres have at least one of the following properties:
- the free surface energy is less than 40 mN/m
- the contact angle of water is greater than 45°, i.e. the wettability is low or absent, the material is hydrophobic
- they cannot be dyed from the aqueous phase
- they can easily become electrostatically charged.

Products made of low-energy synthetic fibres, particularly those made of polyolefins, have several disadvantages:
- the material surfaces are chemically inert; they have no functional groups or only functional groups that can be activated with (chemically) drastic means, so that, for example, dyeing directly from the aqueous phase is not possible.
- the materials easily become electrostatically charged, which prevents any further technical use.
- the materials are not wettable with water. They cannot be used as lining in garments for example, as the inability to absorb perspiration would leave the wearer sweating. They cannot be used for wound dressings/hygiene products as they cannot absorb or convey wound secretions/body fluid. They cannot be used as filter material for aqueous media as the water cannot penetrate the material.

Solutions proposed to overcome the abovementioned disadvantages involve either finishing the surface of low-energy materials with surface-active substances such as wetting agents or surfactants, or depositing hydrophilic polymers such as polyvinyl pyrrolidone or polyvinyl alcohol on the surface. The proposed solutions are not satisfactory as the finishing with surface-active substances is not permanent; they are washed off/out on contact with water. In order for hydrophilic polymers to be retained on the surface, they have to be linked with certain substances, some of which are toxic; this is complicated and costly.

BRIEF SUMMARY OF THE INVENTION

The invention is based on the object of finishing the surface of products made of low-energy synthetic fibres permanently with functional groups, whereby this is achieved essentially with the aid of a well-known chemical which is commercially available as a mass product, and the surface modification can be carried out on an industrial scale. This permanent functionalisation of the material surfaces allows the ionogenic and/or covalent bonding of water-soluble chemicals, e.g. dyes or biologically active compounds, improves the wettability, improves the water absorption and water retention capacity, allows capillary water transport etc., thereby generally enlarging the spectrum of applications for low-energy materials.

The object is solved by bringing products made of low-energy synthetic fibres into contact with a polyvinyl alcohol solution containing silanol(ate) groups and then removing the solvent again.

Polyvinyl alcohol with silanol(ate) groups is well known and commercially available on an industrial scale, see also the technical data sheet "Kuraray R-Polymers" dated November 2007 from the company Kuraray, Frankfurt am Main.

The formula for the polyvinyl alcohol with silanol(ate) groups is:

$$-CH(OH)-CH_2-CH(OAc)-CH_2-CH(Si(ONa)_3)\\-CH_2-CH(OAc)-CH_2-CH(OH)-CH_2-$$

where Ac is acetyl ($CH_3CO-$). According to the technical data sheet the proportion of vinyl acetate groups amounts to 1.5±0.5 mol %. The silanol(ate) groups are bonded to the polymer chain in a hydrolysis-resistant manner by $\equiv C-Si\equiv$ bonds. The acid constant pKa of silanol groups is about pH 4, i.e. when pH<4 there are uncharged silanol ($-Si(OH)_3$) groups; when pH>4 there are negatively charged silanolate ($-Si(O^-)_3$) groups.

It is preferable to use aqueous solutions of polyvinyl alcohol with silanol(ate) groups for permanent surface modification. The concentration of the polymers used depends in particular on the later purpose of the product, and can vary from 0.001% (w/v) to 40% (w/v); generally the concentrations range from 0.01% (w/v) and 10% (w/v). The production of such solutions is known; see, for example, the abovementioned technical data sheet.

Other substances that lower the surface tension of water can be added to these polymer solutions, for example low-aliphatic alcohols, surfactants, wetting agents. Compounds that modify the viscosity of the solution, for example pyrogenic silicic acid or metal salts, can also be added to the solution. Their selection, which is familiar to those skilled in the art, depends on the later purpose of the surface-modified materials, the compatibility with the dissolved modified polyvinyl alcohol, the types of material to be modified, the material properties, the contact and drying conditions.

The pH of the polymer solution used is preferably on the acidic side, at 3±1.

The temperature of the polymer solution used can range from 3° C. to 95° C.; preferably it ranges from 15 to 65° C.; most preferably it is at room temperature.

The low-energy materials are brought into contact with an aqueous solution of polyvinyl alcohol with a silanol(ate) group. The term "contact" here means that the whole surface or certain parts of the surface of the low-energy material are able to enter into physical-chemical interactions with the substances dissolved in the solution, and includes, on the molecular level, terms such as physisorption and chemisorption and, on the production level, terms such as intimate contact, coating, covering, painting, wetting, impregnating, spraying, immersing etc. Preference is given to known methods used on an industrial scale such as (finishing) baths, foulard, squeegee, kiss roll, application roller, WEKO® rotor moistening etc.

The contact duration of the low-energy materials with the polymer solution can range between seconds and several days, and is determined and optimised on the basis of the polymer concentration used, the later purpose of the material, its properties such as texture, compactness, area density etc. as well as economic aspects.

After the low-energy materials have been contacted with the polymer solution, the solvent, preferably water, is removed, which usually takes place by drying the materials covered with the polymer solution. The drying temperatures can range between 1° C. to over 170° C. They are determined on a case-to-case basis, depending on the later purpose and the properties of the material used. Preferably they are at room temperature, especially preferably between 30° C. and 70° C., and most preferably between 70° C. and 130° C. The degree of drying depends on the later purpose of the materials, so that these can have a residual moisture between 0% and 40% with reference to non-surface-modified materials.

A surprising result of the contacting of low-energy materials with aqueous solutions of polyvinyl alcohol with a silanol(ate) group followed by drying was that materials treated in this way could be dyed with a water-soluble dye for cotton (trade name Simplicol®, Brauns-Heitmann, Warburg) and that the dye did not wash out even after intensive washing in hot water. This is taken as proof of the permanent presence of functional groups, in this case hydroxyl (—OH) groups, on the surface of the material. In accordance with the invention, therefore, the inert surface of a synthetic fibre receives the chemical-reactive properties of cellulose fibres, so that we can speak of "synthetic cellulose" or "synthetic cotton".

It is assumed that the contacting described above and the subsequent drying has the effect that the polyvinyl alcohol molecules functionalised with silanol(ate) groups are first enriched on the surface of the synthetic fibres as the solvent, i.e. water, evaporates. As the process advances, the silanol (ate) groups then react (due to condensation reaction and mainly on the intermolecular level with separation of water) with each other, forming a giant molecule that firmly envelopes the surface of the material like a film of paint. Through targeted adjustment of the concentration of the polyvinyl alcohol solution with silanol(ate) groups, it is possible to apply both thin, possibly even monomolecular layers to the surface, but also thick films which firmly connect the individual fibres or close gaps in the mesh or weave.

In a further step, water-soluble substances can be covalently bonded to the functional hydroxyl (—OH) groups firmly bonded in this way to the surface, via ester or acetal or urethane or ether bonds. The esterification can be carried out with organic or inorganic acids. For example, the —OH groups can be esterified with di-, tri- or polycarboxylic acids so that the material surface is negatively, anionically charged in aqueous solution. By esterifying with zwitterions, e.g. amino acids, the surface receives a cationic, positive charge which can be used for further reactions; see example 3. Compounds containing aldehyde groups such as glyceraldehyde, can be added to the —OH groups with acid catalysation to form an acetal bond; in this case the number of —OH groups on the material surface is increased. Double-bonded compounds, e.g. 5-pentenoic acid can be added to the —OH groups with peroxide catalysation to form hydrolysis-stable ether bonds. In this case the surface, at pH>5, receives a negative anionic charge due to the —COO groups. These additional surface modifications shift the spectrum of applications for such surface-modified, low-energy materials from textile applications right up to applications in medicine and biotechnology.

DETAILED DESCRIPTION OF THE EMBODIMENTS

The surface-modified products made of low-energy synthetic fibres surface-modified according to the method of the present invention can be used as filament or fibre material for textile fabrics, as textile fabrics, as textile fabrics that can be dyed with water-soluble dyes, as geotextile fabrics, as filter materials, as wound dressings, as hygiene articles, as substrates for the immobilisation of biologically active substances, as cell cultivation substrates, as substrates that can be metallised, as sinkable fishing line etc.

Example 1

The polyvinyl alcohol with silanol(ate) groups used is R-Polymer R-1130 from the company Kuraray in Frankfurt.

Solution: For the surface-modification of low-energy materials, a 1% (w/v) aqueous R-1130 solution is used, which is produced as follows: 10 g of R-Polymer is added to 1,000 ml of de-ionized water at room temperature and then heated up to 90° C. with constant stirring until the polymer is fully dissolved. The pH is adjusted to 3 with diluted acetic acid.

Material: fibre composite material: polypropylene spunbond with 10, 20 and 30 g/m2 area density from the company Fiberweb Corovin, Peine.

Contact: ca. 5 A4-sized sheets of spunbond are placed on top of each other in a suitable tray and approx. 100 ml of the abovementioned R-Polymer solution is poured over them. Due to the hydrophobic nature of the spunbond material, the solution does not penetrate it, but beads off. A thorough, bubble-free penetration of the polymer solution is only possible with the aid of a squeezer (equivalent to the foulard in an industrial application).

Drying: the dripping wet spunbond sheets are hung on a washing line and dried at room temperature.

Result: compared with untreated non-wovens, the spunbond can be soaked with water again and again even after repeated drying. The dried sheets feel substantially stiffer at the bottom than at the top where they were fixed to the washing line with clothes pegs. This difference in the grip is much more pronounced in the 35 g/m2 spunbond than in the others, and is even retained after several washes.

There is a significant dyeing with Simplicol® which is not washed out (Simplicol®: dye for dyeing cotton from the company Brauns-Heitmann, Warburg, Germany)—untreated control samples do not take the dye.

Example 2

Solution: as in Example 1 but with additional 2% (v/v) 2-propanol

Material: fibre composite material: A4-sized needle felt sheets of polypropylene, Sawatex® 11311Di52 25 g/m2 from the company Sandler, Schwarzenbach.

Contact: manual, similar to Example 1 but without the squeezer as the material is immediately completely wet through due to the added 2-propanol.

Drying: as Example 1.

Result (WSP test method, always compared with the untreated control sample):

maximum water absorption: 1,200 vs. 485 permeation time, 3 cycles (repeated strike through): always <4 seconds vs. >40 seconds.

Readily dyed with Simplicol®, untreated control sample does not take the dye.

Example 3

Solution: as Example 1 with the addition of 0.25% (v/v) Silastan RN Neu® (a wetting agent from the company Schill and Seilacher, Böblingen).

Material: fibre composite material: a non-woven material with an area density of 45 g/m2 and 900 mm width produced on the pilot plant of the company Trützschler, Egelsbach by water jet linking of staple fibres of polypropylene. The production of the non-woven fabric and its contact with polymer solution and drying took place at varying speeds of the plant between 30 and 100 m/min.

Contact: in-line, immediately after production of the non-woven material using a spraying system from the company Weko Biel AG, CH-Biel.

Drying: in-line, immediately after the contact by means of an industrial drying oven at a drying temperature of 110° C.

Result: on contact with water, the non-woven material is immediately saturated and sinks in the water. After repeated washing with water followed by drying, the water absorption slows down but is retained.

The bonded hydroxyl (—OH) groups can always be detected by dyeing with Simplicol®, whereby materials produced at lower machine speeds are more intensively dyed.

The material can be readily dyed with the cationic dye pyronin G. This is attributed to the fact that silanol groups which did not participate in the condensation are now, on being dyed at pH 7, anionic silanolate (—Si(O3)) groups which bind the cationic dye ionogenically.

The hydroxyl (—OH) groups were esterified with betaine (=contacting the material overnight with a 2.5% (w/v) aqueous betaine solution, pH 3). Then anionic compounds such as copper(II) phthalocyanine-tetrasulfonic acid tetrasodium salt link from the aqueous phase with the unbounded cationic trimethyl ammonium groups of the betaine.

Example 4

Solution: as in Example 3.

Material: essentially 1-dimensional synthetic fibre: 722 filaments of polypropylene with 2.7 dtex and a length in the kilometer range, produced on the pilot plant of the company Fibervisions, DK-Varde by melt spinning.

Contact: immediately after leaving the spinneret, the 722 filaments are led continuously at production speed through a bath containing the solution, and then joined to form a "small tow" and wound.

Drying: wound as "small tow", at room temperature, drying time: several days

Results: Positive dyeing with Simplicol®.

Significant capillary effect: one end of a "small tow" immersed in (dyed) water draws the water over a distance of around 300 mm vertically upwards within 24 hours.

Example 5

Solution: as in Example 2.

Material: filament composite material: T-shirt made of polyethylene terephthalate Contact: manual, bubble-free fulling of the solution Drying: manual wringing and hung on clothes line at room temperature Results: compared with the untreated control sample, the T-shirt dries much more slowly even after repeated washing.

The invention claimed is:

1. A method for surface modification of a product made of fibres having a surface, wherein the fibres consist of low-energy synthetic fibres having a free surface energy of less than 40 mN/m, the method comprising the steps of contacting the product with an aqueous solution having a pH of between 2 and 5, the aqueous solution comprising polyvinyl alcohol having silanol(ate) groups and water as a solvent, and then removing the solvent from the products, wherein the silanol(ate) groups are reacted with each other by condensation reaction to form a functionalized fibre surface having hydroxyl groups.

2. The method according to claim 1, wherein the polyvinyl alcohol having silanol(ate) groups comprises the formula —CH(OH)—CH$_2$—CH(OAc)—CH$_2$—CH(Si(ONa)$_3$)
—CH$_2$—CH(OAc)—CH$_2$—CH(OH)—CH$_2$— wherein Ac is acetyl.

3. The method according to claim 1, wherein a concentration of the polyvinyl alcohol having silanol(ate) groups in the solution ranges from 0.001% (w/v) to 40% (w/v).

4. The method according to claim 1, wherein the aqueous solution comprising polyvinyl alcohol having silanol(ate) groups contains other substances that influence at least one of surface tension and viscosity of the aqueous solution.

5. The method according to claim 1, wherein the method comprises the step of contacting all or part of the surface with the aqueous solution comprising polyvinyl alcohol having silanol(ate) groups.

6. The method according to claim 5, wherein the contact is effected manually.

7. The method according to claim 5, wherein the step of contacting takes place with the aid of machines, in-line and at production speed.

8. The method according to claim 1, wherein the step of removing the solvent from the products comprises drying.

9. The method according to claim 8, wherein the drying takes place at a temperature of between 1° C. and 130° C.

10. The method according to claim 8, wherein the drying is carried out at room temperature on a washing line.

11. The method according to claim 8, wherein the drying is carried out with the aid of mechanical aids and in-line at production speed.

12. The method according to claim 8, wherein the products have a residual moisture of between 0% and 40% after drying.

13. The method according to claim 1, wherein the low-energy synthetic fibres consist of a material selected from the group consisting of aramids, polyesters, polyamides, polyacrylates, polyacrylonitriles, polyurethanes, (per)fluorinated polyolefins, polysulfones, polyimides and polyolefins, and co- or terpolymers thereof.

14. The method according to claim 1, wherein the product is selected from the group consisting of filaments, monofilaments, multifilaments, fibres, threads, yarns, strings and rovings.

15. The method according to claim 1, wherein the product is selected from the group consisting of a filament composite material, a fibre composite material and combinations thereof.

16. The method according to claim 1, wherein the product is configured as an article selected from the group consisting of a sinkable fishing line, a means of conveyance for water, a raw material for textile fabrics, a textile fabric, a filter material for aqueous media, a blood and body fluid-absorbing wound dressing, a moisture-absorbent and permeable hygienic article, a substrate for the immobilisation of biologically active substances, a cell cultivation substrate, and substrate for non-electric metallisation.

17. The method of claim 1 wherein the step of removing the solvent comprises reacting the silanol(ate) groups with each other by condensation reaction to form a condensed molecule enveloping the fibre surface.

18. A method for surface modification of a product made of fibres having a surface, wherein the fibres consist of low-energy synthetic fibres having a free surface energy of less than 40 mN/m, the method comprising the steps of:
   providing an aqueous solution having a pH of between 2 and 5 and consisting essentially of polyvinyl alcohol having silanol(ate) groups and water as a solvent, and optionally one or more of aliphatic alcohols, surfactants, wetting agents, pyrogenic silicic acid and metal salts;
   contacting the product with the aqueous solution; and
   removing the solvent from the product to form a functionalized fibre surface having hydroxyl groups.

* * * * *